United States Patent [19]

Mansour et al.

[11] Patent Number: 6,156,737
[45] Date of Patent: Dec. 5, 2000

[54] USE OF DIDEOXY NUCLEOSIDE ANALOGUES IN THE TREATMENT OF VIRAL INFECTIONS

[75] Inventors: Tarek Mansour, Montreal, Canada; Allan H.L. Tse, San Francisco, Calif.

[73] Assignee: BioChem Pharma Inc., Laval, Canada

[21] Appl. No.: 08/416,746

[22] PCT Filed: Dec. 22, 1993

[86] PCT No.: PCT/CA93/00563

§ 371 Date: Apr. 12, 1995

§ 102(e) Date: Apr. 12, 1995

[87] PCT Pub. No.: WO94/14456

PCT Pub. Date: Jul. 7, 1994

[30] Foreign Application Priority Data

Dec. 24, 1992 [GB] United Kingdom .................. 9226927

[51] Int. Cl.[7] .......................... A61K 31/70; A01N 43/04; C07H 19/00
[52] U.S. Cl. .............................. 514/49; 514/50; 514/885; 514/894; 536/27.14; 536/28.2
[58] Field of Search .............................. 514/49, 50, 885, 514/894; 536/27.14, 28.2

[56] References Cited

U.S. PATENT DOCUMENTS

| | | | |
|---|---|---|---|
| 4,724,232 | 2/1988 | Rideout et al. | 514/50 |
| 4,788,181 | 11/1988 | Driscoll et al. | 514/49 |
| 5,039,667 | 8/1991 | Tyrrell et al. | 514/45 |
| 5,179,104 | 1/1993 | Chu et al. | 544/310 |
| 5,409,906 | 4/1995 | Datema et al. | 514/49 |
| 5,631,239 | 5/1997 | Lin et al. | 514/49 |
| 5,744,596 | 4/1998 | Masour et al. | 536/27.11 |
| 5,756,706 | 5/1998 | Masour et al. | 536/27.11 |

FOREIGN PATENT DOCUMENTS

| | | |
|---|---|---|
| 0 206 497 | 12/1986 | European Pat. Off. . |
| 0 285 884 | 10/1988 | European Pat. Off. . |
| 0 302 760 B1 | 2/1989 | European Pat. Off. . |
| 0 352 248 | 1/1990 | European Pat. Off. . |
| 0 494 119 A1 | 7/1992 | European Pat. Off. . |
| 0 515 144 | 11/1992 | European Pat. Off. . |
| WO 90/14079 | 11/1990 | WIPO . |
| WO 91/01137 | 2/1991 | WIPO . |
| WO 91/17159 | 11/1991 | WIPO . |
| WO 92/11852 | 7/1992 | WIPO . |
| WO 92/14743 | 9/1992 | WIPO . |
| WO 92/15308 | 9/1992 | WIPO . |
| WO 92/18517 | 10/1992 | WIPO . |
| WO 92/20696 | 11/1992 | WIPO . |
| WO 93/03027 | 2/1993 | WIPO . |

OTHER PUBLICATIONS

J. Balzarini et al., "Potent and Selective Anti–HTLV–III/LAV Activity of 2', 3'–Dideoxycytidinene, The 2', 3'–Unsaturated Derivative of 2', 3'–Unsaturated Derivative of 2', 3'–Dideoxycytine," *Biochem. Biophys. Res. Commun.*, 140, pp. 735–742 (1986).

S. Doong et al., "Inhibition of the Replication of Hepatitis B Virus In Vitro By 2', 3'–Dideoxy–3'–Thiacytidine and Related Analogues," *Proc. Natl. Acad. Sci.*, 88, pp. 8495–8499 (1991).

F.A. Farraye et al., "Preliminary Evidence That Azidothymidine Does Not Affect Hepatitis B Virus Replication in Acquired Immunodeficiency Syndrome (AIDS) Patients," *J. Med. Virol.*, 29, pp. 266–267 (1989).

H. Haritani et al., "Effect of 3'–Azido–3'–Deoxythymidine On Replication of Duck Hepatitis B Virus In Vivo and In Vitro," *J. Med. Virol.*, 29, pp. 244–248 (1989).

C. Kassianides et al., "Effects of 2', 3'–Dideoxycytidine On Duck Hepatitis B Virus," *Gastroenterology*, 94, Abstract A552 (1988).

C. Kassianides et al., "Inhibition of Duck Hepatitis B Virus Replication by 2', 3'–Dideoxycytidine: A Potent Inhibitor of Reverse Transcriptase," *Gastroenterology*, 97, pp. 1275–1280 (1989).

C. Kim et al., "Potential Anti–AIDS Drugs: 2', 3'–Dideoxycytidine Analogues," *J. Med. Chem.*, 30, pp. 862–866 (1987).

M. Mansuri et al., "1–(2, 3–Dideoxy–β–D–glycero–pent–2–enofuranosyl) thymine. A Highly Potent and Selective Anti–HIV Agent," *J. Med. Chem.*, 32, pp. 461–466 (1989).

H. Mitusya et al., "Inhibition of The In Vitro Infectivity and Cytopathic Effect of Human T–Lymphotrophic Virus Type III/Lymphadenopathy–Associated Virus (HTLV–III/LAV) by 2', 3'–Dideoxynucleosides," *Proc. Natl. Acad. Sci.*, 83, pp. 1911–1915 (1986).

Siddiqui et al., "Chemistry and Anti–HIV Properties of 2'–Fluoro–2', 3'–dideoxyarabinofuranosylpyrimidines," *J. Med. Chem.*, 35, pp. 2195–2201 (1992).

S. Suzuki et al., "Inhibition of Duck Hepatitis B Virus Replication By Purine 2', 3'–Dideoxynucleosides," *Biochem. Biophys. Res. Commun.*, 156, pp. 1144–1151 (1988).

T. Yokota et al., "Comparative Activities of Several Nucleoside Analogs Against Duck Hepatitis B Virus In Vitro," *Antimicrob. Agents Chemotherap.*, 34, pp. 1326–1330 (1990).

M. Baba et al., "Both 2', 3'–Dideoxythymidine and its 2', 3'–Unsaturated Derivative (2', 3'–Dideoxythymidinene) are Potent and Selective Inhibitors of Human Immunodeficiency Virus Replication In Vitro", *Biochem. Biophys. Res. Commun.*, 142, pp. 128–134 (1987).

J.W. Beach et al., "Synthesis of Enantiomerically Pure (2'R,5'S)–(–)–1–[2–(Hydroxymethyl)oxathiolan–5–yl]cytosine as a Potent Antiviral Agent Against Hepatitis B Virus (HBV) and Human Immunodeficiency Virus (HIV)", *J. Org. Chem.*, 57, pp. 2217–2219 (1992).

(List continued on next page.)

*Primary Examiner*—James O. Wilson
*Attorney, Agent, or Firm*—Millen, White, Zelano & Branican, P.C.

[57] ABSTRACT

The present invention is directed to a method of treating hepatitis B viral infections in mammals comprising the administration of β-L-5-fluoro-2',3'-dideoxycytidine and pharmaceutically acceptable derivatives thereof.

29 Claims, No Drawings

OTHER PUBLICATIONS

J.M. Cameron et al., "Lamivudine", *Drugs of the Future*, 18, pp. 319–323 (1993).

C.-N. Chang et al., "Deoxycytidine Deaminase–resistant Steroisomer Is the Active Form of (+/−)-2', 3'-Dideoxy-3'-Thiacytidine in the Inhibition of Hepatitis B Virus Replication", *J.Biol. Chem.*, 267, pp. 13938–13942 (1992).

K.J. Connolly and S.M. Hammer, "Antiretroviral Therapy: Reverse Transcriptase Inhibition", *Antimicrob. Agent Chemother.*, 36, pp. 2686–2692 (1992).

P.A. Furman et al., "The Anti–Hepatitis B Virus Activities, Cytotoxicites, and anabolic Profiles of the (−) and (+) Enantiomers of cis–5–Fluoro–1–[2-(Hydroxymethyl)–1, 3–Oxathiolan–5–yl]Cytosine", *Antimicrob. Agents Chemther.*, 36, pp. 2686–2692 (1992).

P. Herdewijn et al., "3'–Substituted 2', 3'–Dideoxynucleoside Analogues as Potential Anti–HIV (HTLV–III/LAV) Agents", *J. Med. Chem.*, 30, pp. 1270–1278 (1987).

P. Herdewijn and E. De Clercq, "Dideoxynucleoside Analogues as Inhibitors of HIV Replication" *Design of Anti–AIDS Drugs*, E. De Clercq, Ed., pp. 141–174 (Elsevier, 1990).

C.-H. Kim et al., "Potential Anti–AIDS Drugs. 2', 3'-Dideoxycytidine Analogues", *J. Med. Chem.*, 30, pp. 862–866 (1987).

B.E. Korba and G. Milman, "A Cell Culture Assay for Compounds which Inhibit Hepatitus B Virus Replication", *Antiviral Res.*, 15, pp. 217–228 (1991).

B. Lee et al., "In Vitro and In Vivo Comparison of the Abilities of Purine and Pyrimidine 2', 3'–Dideoxynucleosides to Inhibit Duck Hepadnavirus", *Antimicrob. Agents Chemther.*, 33, pp. 336–339 (1989).

T.-S. Lin et al., "Synthesis and Biological Evaluation of 2', 3'-Dideoxy-L-Pyrimidine Nucleosides as Potential Antiviral Agents Against HIV and HBV", *207th American Chemical Society Natioinal Meeting*, San Diego, CA, USA, Mar. 13–Mar. 17, Program Abstract MEDI 31 (1994).

T.-S. Lin et al., "Synthesis and Antiviral Activity of Various 3'–Azido, 3'–Amino, 2', 3'–Unsaturated, and 2', 3'–Dideoxy Analogues of Pyrimidine Deoxyribonucleosides against Retroviruses", *J. Med. Chem.*, 30, 440–444 (1987).

M.M. Mansuri et al., "Preparation of the Geometric Isomers of DDC, DDA, D4C and D4T as Potential Anti–HIV Agents", *Bioorg. Med. Chem. Lett.*, 1, pp. 65–68 (1991).

M. Okabe et al., "Synthesis of the Dideoxynucleosides ddC and CNT from Glutamic Acid, Ribonolactone, and Pyrimidine Bases" *J. Org. Chem.*, 53, pp. 4780–4786 (1988).

M.K. Sachs, "Antiretroviral Chemotherapy of Human Immunodeficiency Virus Infections Other Than With Azidothymidine", *Arch. Intern. Med.*, 152, pp. 485–501 (1992).

R.F. Schinazi et al., "Pure Nucleoside Enantiomers of β-2', 3'-Dideoxycytidine Analogs Are Selective Inhibitors of Hepatitis B Virus In Vitro", *Antimicrob. Agents Chemother.*, 38, pp. 2172–2174 (1994).

R.F. Schinazi et al., "Cellular Pharmacology and Monkey Pharmacokinetics of the Antiviral (−)-2', 3'-Dideoxy-5-Flouro-3'-Thiacytidine [(−)-FTC]", *Thirty–second Interscience Conference of Antimicrobial Agents and Chemotherapy*, Anaheim, CA, USA, Oct. 11–14, 1992, Program Abstract 1321, p. 331 (1992).

R.F. Schinazi et al., "Selective Inhibition of Human Immunodeficiency Viruses by Racemates and Enantiomers of cis–5–Fluoro–1–[2-(Hydroxymethyl)–1, 3–Oxathiolane–5–yl]Cytosine", *Antimicrob. Agents Chemother.*, 36, pp. 2423–2431 (1992).

H.E. Varmus "A Growing Role for Reverse Transcription", *Nature*, 299, pp. 204–205 (1982).

R. Vince & J. Brownell "Resolution of Racemic Carbovir and Selective Inhibition of Human Immunodeficiency Virus by the (−) Enantiomer", *Biochem. Biophys. Res. Commun.*, 168, pp. 912–916 (1990).

J. Wengel et al., "Synthesis of L-3'-Azido-3'-deoxythymidine and Its Steroisomers" *J. Org. Chem.*, 56, pp. 3591–3594 (1991).

USE OF DIDEOXY NUCLEOSIDE ANALOGUES IN THE TREATMENT OF VIRAL INFECTIONS

The present invention relates to nucleoside analogues and their use in medicine. More specifically the invention is concerned with dideoxy nucleoside analogues, pharmaceutical formulations thereof and the use thereof in the treatment of viral infections.

The only compounds currently approved for the treatment of conditions caused by HIV are D-3'-azido-3'-deoxythymidine (AZT, zidovudine, BW 509U) and β-D-2',3'-dideoxyinosine (ddI, didanosine) which has been approved for use in patients who are intolerant to AZT. Also, β-D-2',3'-dideoxycytidine (ddC) has received approval only in combination with AZT. The above compounds derived from physiologically important nucleosides have significant side-effect liability and dose-limiting toxicity. Additionally, resistance to AZT, ddC and ddI has emerged (K. J. Connolly and S. M. Hammer, Antimicrob. Agent. Chemother. 1992; 36, 245–254).

There is, in consequence, a continuing need to provide compounds which are effective against HIV but with a concommitant significantly better therapeutic index (i.e. more selective).

The compounds mentioned above are all used in the form of their natural enantiomers (D sugars). The corresponding unnatural enantiomers of AZT (L-AZT) and ddI (β-L-ddI) have been found to be inactive against HIV (J. Wengel et al. J. Org. Chem, 1991; 56, 3591–3594; and M. M. Mansuri et al. BioMed. Chem. Lett. 1991; 1, 65–68) whereas the unnatural enantiomer of ddC (β-L-ddC) was reported to be inactive or weakly active against HIV (M. Okabe & al. J. Org. Chem. 1988; 54, 4780–4786 and M. M. Mansuri & al. Bio Med. Chem. Lett. 1991; 1, 65–68) with no mention of selectivity. Furthermore, there has been no report in the literature about the activity of β-L-ddC against the Hepatitis B virus (HBV).

We have now found that, surprisingly, β-L-ddC, the unnatural (−)-enantiomer of ddC is active against HIV with unexpectedly high selectivity.

Furthermore, we have also found, unexpectedly, that β-L-ddC possesses excellent activity against Hepatitis B virus.

Moreover, the 5-fluoro analogue of ddC (5F-ddC) has been described and tested in the form of its natural enantiomer (β-D-5F-ddC) and found to be active against HIV (Kim et al., J. Med. Chem. 1987: 30, 862–866). However, its activity against HBV has not been reported.

We have found that the natural enantiomer of 5F-ddC (β-D-5F-ddC) is active against against HBV.

In addition, there has been no reports of the activity of its corresponding unnatural enantiomer (β-L-5F-ddC) against HIV or HBV.

We have also found, unexpectedly, that the unnatural enantiomer of 5F-ddC (β-L-5F-ddC) possesses activity against HIV and HBV below its cytotoxic concentration.

SUMMARY OF THE INVENTION

There is thus provided, in a first aspect of the invention, the use of the (−)-enantiomer of ddC (β-L-ddC) and pharmaceutically acceptable derivatives thereof in the treatment of HIV infection.

There is also provided, in a second aspect of the invention, the use of β-L-ddC and pharmaceutically acceptable derivatives thereof in the treatment of HBV infections.

There is further provided, in a third aspect of the invention, the use of β-D-5F-ddC and pharmaceutically acceptable derivatives thereof in the treatment of HBV infections.

Furthermore, there is provided, in a fourth aspect of the invention, the use of β-L-5F-ddC and pharmaceutically acceptable derivatives thereof for the treatment of HIV infections.

There is also provided, in a fifth aspect of the invention, the use of β-L-5F-ddC and pharmaceutically acceptable derivatives thereof for the treatment of HBV infections.

These compounds are represented by formula (I):

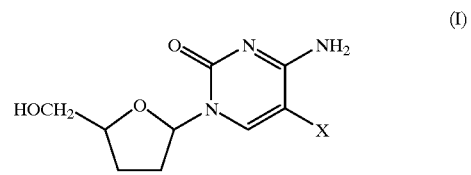

(I)

wherein X is hydrogen or fluoro. The compounds of formula (I) are racemic mixtures of the two enantiomers of formulae (Ia) and (Ib):

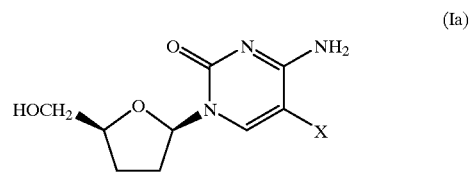

(Ia)

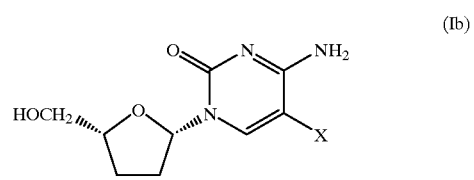

(Ib)

The (−)-enantiomer of ddC has the absolute configuration of 1'S at the carbon bearing the base and 4'R at the carbon bearing the $CH_2OH$ moiety. It has the absolute stereochemistry of the compound of formula (Ib) and the chemical name of β-L-2',3'-dideoxycytidine or (1'S,4'R)-2',3'-dideoxycytidine (hereinafter Compound A). The (+)-enantiomer of 5F-ddC has the absolute stereochemistry of the compound of formula (Ia) and the chemical name of β-D-5-fluoro-2',3'-dideoxycytosine (hereinafter Compound B).

The (−)-enantiomer of 5F-ddC has also the absolute stereochemistry of the compound of formula (Ib) and the chemical name of β-L-5-fluoro-2',3'-dideoxycytosine (hereinafter Compound C).

Preferably compound A or C are provided substantially free of the corresponding (+)-enantiomer, that is to say no more than about 5% w/w of the (+)-enantiomer, preferably no more than about 2%, in particular less than about 1% w/w is present.

Preferably compound B is provided substantially free of the corresponding (−)-enantiomer, that is to say no more than about 5% w/w of the (−)-enantiomer, preferably no more than about 2%, in particular less than about 1% w/w is present.

By "a pharmaceutically acceptable derivative" is meant any pharmaceutically acceptable salt, ester, or salt of such ester, of compound A, B or C or any other compound which, upon admistration to the recipient, is capable of providing (directly or indirectly) compound A, B or C or an antivirally active metabolite or residue thereof.

It will be appreciated by those skilled in the art that compound A, B or C may be modified to provide pharmaceutically acceptable derivatives thereof, at functional groups in both the base moiety and at the hydroxymethyl group of the oxathiolane ring. Modification at all such functional groups are included within the scope of the invention. However of particular interest are pharmaceutically acceptable derivatives obtained by modification of the 2-hydroxymethyl group at 4'-carbon of the sugar ring.

Preferred esters of compound A, B or C include the compounds in which the hydrogen of the 2-hydroxymethyl group is replaced by an acyl function R—C(O)— in which the non-carbonyl moiety R of the ester is selected from hydrogen, straight or branched chain alkyl (e.g. methyl, ethyl, n-propyl, t-butyl, n-butyl), alkoxyalkyl (e.g. methoxymethyl), aralkyl (e.g. benzyl), aryloxyalkyl (e.g. phenoxymethyl), aryl (e.g. phenyl optionally substituted by halogen, $C_{1-4}$ alkyl or $C_{1-4}$ alkoxy); sulphonate esters such as alkyl- or aralkylsulphonyl (e.g. methanesulphonyl); amino acid esters (e.g. L-valyl or L-isoleucyl) and mono-, di- or tri-phosphate esters.

With regard to the above described esters, unless otherwise specified, any alkyl moiety present advantageously contains 1 to 16 carbon atoms, particularly 1 to 4 carbon atoms. Any aryl moiety present in such esters advantageously comprises a phenyl group.

In particular the esters may be a $C_{1-16}$ alkyl ester, an unsubstituted benzyl ester or a benzyl ester substituted by at least one halogen (bromine, chlorine, fluorine or iodine), $C_{1-6}$ alkyl, $C_{1-6}$ alkoxy, nitro or trifluoromethyl groups.

Pharmaceutically acceptable salts of the compound A, B or C include those derived from pharmaceutically acceptable inorganic and organic acids and bases. Examples of suitable acids include hydrochloric, hydrobromic, sulphuric, nitric, perchloric, fumaric, maleic, phosphoric, glycollic, lactic, salicylic, succinic, toleune-p-sulphonic, tartaric, acetic, citric, methanesulphonic, formic, benzoic, malonic, naphthalene-2-sulphonic and benzenesulphonic acids. Other acids such as oxalic, while not in themselves pharmaceutically acceptable, may be useful as intermediates in obtaining the compounds of the invention and their pharmaceutically acceptable acid addition salts.

Salts derived from appropriate bases include alkali metal (e.g. sodium), alkaline earth metal (e.g. magnesium), ammonium and $NR_4+$ (where R is $C_{1-4}$ alkyl) salts.

References hereinafter to a compound according to the invention include, the compound A, B or C and their pharmaceutically acceptable derivatives.

The compounds of the invention either themselves possess antiviral activity and/or are metabolizable to such compounds. In particular these compounds are effective in inhibiting the replication of retroviruses, including human retroviruses such as human immunodeficiency viruses (HIV's), the causative agents of AIDS.

There is thus provided as a further aspect of the invention compound A, B or C or a pharmaceutically acceptable derivative thereof for use as an active therapeutic agent in particular as an antiviral agent, for example in the treatment of retroviral infections or infections by viruses known to possess reverse transcriptase activity (such as Hepatitis B virus).

In a further or alternative aspect there is provided a method for the treatment of a viral infection, in particular an infection caused by a retrovirus such as HIV, or by a virus possessing retroviral activity such as HBV in a mammal including man comprising administration of an effective amount of compound A, B or C or a pharmaceutically acceptable derivative thereof.

There is also provided in a further or alternative aspect use of compound A, B or C or a pharmaceutically acceptable derivative thereof for the manufacture of a medicament for the treatment of a viral infection.

The compounds of the invention are also useful in the treatment of HBV or of AIDS related conditions such as AIDS-related complex (ARC), progressive generalised lymphadenopathy (PGL), AIDS-related neurological conditions (such as dementia or tropical paraparesis), anti-HIV antibody positive and HIV-positive conditions, Kaposi's sarcoma, thrombocytopenia purpura and associated opportunistic infections for example *Pneumocystis carinii.*

The compounds of the invention are also useful in the prevention of progression to clinical illness of individuals who are anti-HIV or HBV antibody or HIV-or HBV-antigen positive and in prophylaxis following exposure to HIV or HBV.

The compound A, B or C or pharmaceutically acceptable derivatives thereof may also be used for the prevention of viral contamination of physiological fluids such as blood or semen in vitro.

It will be appreciated by those skilled in the art that reference herein to treatment extends to prophylaxis as well as the treatment of established infections or symptoms.

It will be further appreciated that the amount of a compound of the invention required for use in treatment will vary not only with the particular compound selected but also with the route of administration, the nature of the condition being treated and the age and condition of the patient and will be ultimately at the discretion of the attendant physician or veterinarian. In general however a suitable dose will be in the range of from about 0.1 to about 750 mg/kg of bodyweight per day preferably in the range of 0.5 to 60 mg/kg/day, most preferably in the range of 1 to 20 mg/kg/day.

The desired dose may conveniently be presented in a single dose or as divided doses administered at appropriate intervals, for example as two, three, four or more sub-doses per day.

The compound is conveniently administered in unit dosage form; for example containing 10 to 1500 mg, conveniently 20 to 1000 mg, most conveniently 50 to 700 mg of active ingredient per unit dosage form.

Ideally the active ingredient should be administered to achieve peak plasma concentrations of the active compound of from about 1 to about 75 $\mu$M, preferably about 2 to 50 $\mu$M, most preferably about 3 to about 30 $\mu$M. This may be achieved, for example, by the intravenous injection of a 0.1 to 5% solution of the active ingredient, optionally in saline, or orally administered as a bolus containing about 1 to about 100 mg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

While it is possible that, for use in therapy, a compound of the invention may be administered as the raw chemical it is preferable to present the active ingredient as a pharmaceutical formulation.

The invention thus further provided a pharmaceutical formulation comprising compound A, B or C or a pharmaceutically acceptable derivative thereof together with one or more pharmaceutically acceptable carriers therefor and, optionally, other therapeutic and/or prophylactic ingredients. The carrier(s) must be 'acceptable' in the sense of being compatible with the other ingredients of the formulation and not deleterious to the recipient thereof.

Pharmaceutical formulations include those suitable for oral, rectal, nasal, topical (including buccal and sub-lingual), vaginal or parenteral (including intramuscular, subcutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical formulations suitable for oral administration may conveniently be presented as discrete units such as capsules, cachets or tablets each containing a predetermined amount of the active ingredient; as a powder or granules; as a solution, a suspension or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, emulsiying agents, non-aqueous vehicles (which may include edible oils), or preservatives.

The compounds according to the invention may also be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilising and/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

For topical administration to the epidermis the compounds according to the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Formulations suitable for topical administration in the mouth include lozenges comprising active ingredient in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical formulations suitable for rectal administration wherein the carrier is a solid are most preferably presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

Formulations suitable for vaginal administration may be presented as pessaries, tampons, creams, gels, pastes, foams or sprays containing in addition to the active ingredient such carriers as are known in the art to be appropriate.

For intra-nasal administration the compounds of the invention may be used as a liquid spray or dispersible powder or in the form of drops.

Drops may be formulated with an aqueous or non-aqueous base also comprising one more more dispersing agents, solubilising agents or suspending agents. Liquid sprays are conveniently delivered from presurrised packs.

For administration by inhalation the compounds according to the invention are conveniently delivered from an insufflator, nebuliser or a pressurised pack or other convenient means of delivering an aerosol spray. Pressurised packs may comprise a suitable propellant such as dichlorodifluoromethane, trichlorofluoromethane, dichlorotetrafluoroethane, carbon dioxide or other suitable gas. In the case of a presurrised aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges or e.g. gelatin or blister packs from which the powder may be administered with the aid of an inhalator or insufflator.

When desired the above described formulations adapted to give sustained release of the active ingredient may be employed.

The pharmaceutical compositions according to the invention may also contain other active ingredients such as antimicrobial agents, or preservatives.

The compounds of the invention may also be used in combination with other therapeutic agents for example other antiinfective agents. In particular the compounds of the invention may be employed together with known antiviral agents.

The invention thus provides, in a further aspect, a combination comprising the compound A, B or C or a physiologically acceptable derivative thereof together with another therapeutically active agent, in particular an antiviral agent.

The combinations referred to above may conveniently be presented for use in the form of a pharmaceutical formulation and thus pharmaceutical formulations comprising a combination as defined above together with a pharmaceutically acceptable carrier therefor comprise a further aspect of the invention.

Suitable therapeutic agents for use in such combinations include acyclic nucleosides such as acyclovir or ganciclovir, interferons such as $\alpha$, $\beta$ or $\gamma$-interferon, renal excretion inhibitors such as probenecid, nucleoside transport inhibitors such as dipyridamole, 1,3-oxathiolane nucleoside analogues, such as 3TC, 2',3'-dideoxynucleosides such as AZT, 2',3'-dideoxyadenosine, 2',3'-dideoxyinosine, 2',3'-dideoxythymidine, 2',3'-dideoxy-2'3'-didehydrothymidine and 2',3'-dideoxy-2',3'-didehydrocytidine, FIAU, immunomodulators such as interleukin II (IL2) and granulocyte macrophage colony stimulating factor (GM-CSF), erythropoetin, ampligen, thymomodulin, thymopentin, foscarnet, ribavirin, and inhibitors of HIV binding to CD4 receptors e.g. soluble CD4, CD4 fragments, CD4 hybrid molecules, glycosylation inhibitors such as 2-deoxy-D-glucose, castanospermine and 1-deoxynojirimycin.

The individual components of such combinations may be administered either sequentially or simultaneously in separate or combined pharmaceutical formulations.

When the compound A, B or C or a pharmaceutically acceptable derivative thereof is used in combination with a second therapeutic agent active against the same virus the dose of each compound may be either the same as or differ from that when the compound is used alone. Appropriate doses will be readily appreciated by those skilled in the art.

The compound A, B or C and their pharmaceutically acceptable derivatives may be prepared by any method known in the art for the preparation of compounds of analogous structure, for example as described in international publication No. WO 92/20969 which is herein incorporated by reference.

It will be appreciated by those skilled in the art that for certain of the methods the desired stereochemistry of the compound A, B or C may be obtained either by commencing with an optically pure starting material or by resolving the racemic mixture at any convenient stage in the synthesis. In the case of all the processes the optically pure desired product may be obtained by resolution of the end product of each reaction.

EXAMPLE 1

Antiviral activity & Cytotoxicity

A) MT-4 Formazan assay

Antiviral activity was determined in MT-4 cells by inhibition of formazan conversion (Baba & al., (1987) Biochem. Biophys. Res. Commun. 142, 128–134; Mossman (1983) J. Immun. Meth.; 65, 55–57).

B) Inhibition of Syncytium Formation Assay

C8166 cells were infected with HIV-1 (strain RF) at a moi of $1\times10^{-3}$ infectious units/cell and adsorbed at room temperature for 60 minutes. After adsorption, the cells were washed three times in growth medium. Aliquots of $10^5$ cells were added to each well of 24-well plates containing serial dilutions of test compounds at final concentrations of 50 μg/ml to 0.05 μg/ml in RPMI® 1640 growth medium. Untreated infected cells and untreated uninfected cells were also included as controls. The plates were incubated at 37° C./5% $CO_2$ for 3–4 days in humidified containers. The cells were examined daily for evidence of HIV-1 induced syncytium formation. The syncytia were quantified by reference to the untreated infected controls, and the dose of compound required to reduce the cytopathic effect by 50% ($ID_{50}$) was calculated.

C) Cytotoxicity

The cytotoxicities of the compounds were determined in five CD4 cell lines: H9, JM, CEM, C8166 and U937.

Compounds for test were serially diluted from 100 μg/ml to 0.3 μg/ml (final concentrations) in 96 well microtitre plates. $3.6\times10^4$ cells were inoculated into each well of the plates including drug-free controls. After incubation at 37° C. for 5 days, the viable cell count was determined by removing a sample of cell suspension and counting trypan blue excluding cells in a haemocytometer.

Results are shown in Table 1.

D) Inhibition of Human Hepatitis B virus.

The method used for this test is described in detail in Korba et al., Antiviral Research 15, 217–228 (1992) which is shortly described as follows:

Hep G2 cells transfected with human hepatitis B virus genomic DNA (2.2.15 cells) were grown and maintained in RPMI-1640 culture medium containing %5 foetal bovine serum, 2 mM glutamine and 50 μg/ml gentamicin sulphate, and checked routinely for G418 resistance. Cultures of 2.2.15 cells were grown to confluence in 24 well tissue culture plates and maintained for 2 to 3 days in that condition prior to drug treatment.

Drugs were dissolved in sterile water or sterile 50% DMSO in water at concentrations 100-fold higher than the higher test concentration. These solutions were diluted as needed in culture medium.

The culture medium on the confluent cells was changed 24 hours prior to exposure to test compounds. During the 10 day treatment, the culture medium was changed daily. After 10 days of the treatment, the culture medium was collected and frozen at −70° C. for HBV DNA analysis.

To analyse extracellular HBV DNA, 0.2 ml samples of culture medium were incubated for 20 minutes at 25° C. in 1M NaOH/10× SSC (1× SSC is 0.15M NaCl/0.015M Sodium Citrate, pH 7.2) and then applied to nitrocellulose membranes presoaked in 20× SSC. Filters were then rinsed in 2× SSC and baked at 80° C. for 1 hour under vacuum.

A purified 3.2 kb EcoR1 HBV DNA fragment was labelled with [$^{32}$P]dCTP by nick translation and used as a probe to detect HBV DNA on the dot-blot by DNA hybridisation. After washing, the hybridised blot was dried and 32P was quantified using an Ambis beta scanner.

Results are shown in Table 2.

TABLE 1

| | 50% Antiviral Activity against HIV in μg/ml (μM) | | | |
|---|---|---|---|---|
| | Formazan | | Syncytium Formation | |
| Assay | Antiviral | Cytotoxicity | Antiviral | Cytotoxicity |
| AZT (natural) | 0.0022 (0.0092) | >1 | 0.002 (0.0084) | >0.5 |
| A) β-L-ddC (−) (unnatural) | 0.022 (0.1) | >100 (>474) | 0.014 (0.067) | >5 (>24) |
| B) β-D-5F-ddC (+) (natural) | 0.145 (0.63) | 10 (44) | 0.0056 (0.02) | >0.5 (>2.2) |
| C) β-L-5F-ddC (−) (unnatural) | 0.05 (0.22) | 1 (4.4) | 0.011 (0.05) | >0.5 (>2.2) |

TABLE 2

| | 50% Antiviral Activity against HBV in μg/ml | |
|---|---|---|
| | Hepatitis B Virus | |
| Assay | Antiviral | Cytotoxicity |
| AZT | | |
| A) β-L-ddC (−) (unnatural) | 0.44 | >10 |
| B) β-D-5F-ddC (+) (natural) | <10 | >10 |
| C) β-L-5F-ddC (−) (unnatural) | <10 | >10 |

We claim:

1. A method for the treatment of hepatitis B viral infections in mammals comprising the step of administering a pharmaceutically effective amount of a β-L enantiomer of formula (Ib):

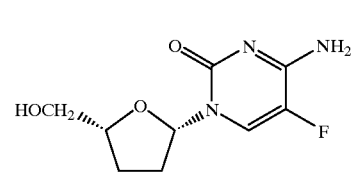

or pharmaceutically acceptable derivatives thereof.

2. A method for the treatment of hepatitis B viral infections in mammals comprising the step of administering a pharmaceutically effective amount of a mixture of the β-L-enantiomer of formula (Ib) and the β-D-enantiomer of formula (Ia):

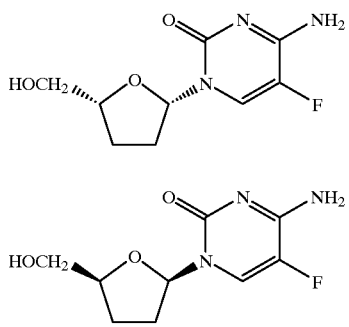

wherein said mixture contains no more than about 5% w/w of the β-D-enantiomer.

3. The method according to claim 2 wherein said mixture contains no more than about 2% w/w of the β-D-enantiomer.

4. The method according to claim 2 wherein said mixture contains no more than about 1% w/w of the β-D-enantiomer.

5. The method according to claim 1, wherein said administration is carried out at a dose of about 0.1 to at least 750 mg/kg of body weight per day.

6. The method according to claim 5 wherein said administration is carried out at a dose of about 0.5 to at least 60 mg/kg of body weight per day.

7. The method according to claim 6, wherein said administration is carried out at a dose of about 1.0 to at least 20 mg/kg of body weight per day.

8. The method according to claim 1, wherein said enantiomer is administered in dosage unit form.

9. The method according to claim 8 wherein said enantiomer is administered in dosage unit form in the amount of about 10 to 1500 mg.

10. The method according to claim 9 wherein said enantiomer is administered in dosage unit form in the amount of about 20 to 1000 mg.

11. The method according to claim 10 wherein said enantiomer is administered in dosage unit form in the amount of about 50 to 700 mg.

12. The method according to claim 5 wherein said administration is carried out in admixture with a pharmaceutically acceptable carrier.

13. The method according to any one of claims 6, 7, 9, 10 or 11 wherein said administration is carried out in admixture with a pharmaceutically acceptable carrier.

14. The method according to claim 8, wherein said administration is carried out in admixture with a pharmaceutically acceptable carrier.

15. The method according to claim 12 or 14 wherein said administration is carried out with another therapeutically active agent.

16. The method according to claim 13 wherein said administration is carried out with another therapeutically active agent.

17. The method according to claim 15 wherein said therapeutically active agent is an antiviral agent.

18. The method according to claim 16 wherein said therapeutically active agent is an antiviral agent.

19. The method according to claim 17 and 18 wherein said antiviral agent is AZT.

20. The method according to claim 18 wherein said antiviral agent is (−)-2'-deoxy-3'-thiacytidine.

21. The compound, β-L-5-fluoro-2',3'-dideoxycytidine, and pharmaceutically acceptable derivatives thereof.

22. A mixture of β-L-5-fluoro-2',3'-dideoxycytidine and β-D-5-fluoro-2',3'-dideoxycytidine wherein the β-D-enantiomer is present in an amount of no more than about 5% w/w.

23. The mixture according to claim 22 wherein the β-D-enantiomer is present in an amount of no more than about 2% w/w.

24. The mixture according to claim 22 wherein the β-D-enantiomer is present in an amount of no more than about 1% w/w.

25. A pharmaceutical composition comprising a therapeutically effective amount of the compound of claim 21 in combination with a pharmaceutically acceptable additive, carrier or excipient.

26. A pharmaceutical composition comprising a therapeutically effective amount of the mixture of any of claims 22, 23 or 24 in combination with a pharmaceutically acceptable additive, carrier or excipient.

27. The compound 1-(2,3-Dideoxy-beta-L-ribofuranosyl)-5-fluorocytosine.

28. A pharmaceutical composition comprising a therapeutically effective amount of the compound 1-(2,3-Dideoxy-beta-L-ribofuranosyl)-5-fluorocytosine in combination with a pharmaceutically acceptable additive, carrier or excipient.

29. A method of treating an HBV infection in a patient comprising administering to said patient a therapeutically effective amount of the compound 1-(2,3-Dideoxy-beta-L-ribofuranosyl)-5-fluorocytosine.

* * * * *